(12) United States Patent
Lin et al.

(10) Patent No.: US 12,090,182 B2
(45) Date of Patent: Sep. 17, 2024

(54) METHOD FOR PREVENTING OR ALLEVIATING PARTICULATE MATTER-INDUCED LUNG INJURY

(71) Applicant: CHAMBIO CO., LTD., Taichung (TW)

(72) Inventors: Meei-Yn Lin, Taichung (TW); Hung-Pin Chiu, Taichung (TW); Yi-Heng Chiu, Taichung (TW)

(73) Assignee: CHAMBIO CO., LTD., Taichung (TW)

( * ) Notice: Subject to any disclaimer, the term of this patent is extended or adjusted under 35 U.S.C. 154(b) by 0 days.

(21) Appl. No.: 17/529,474

(22) Filed: Nov. 18, 2021

(65) Prior Publication Data

US 2023/0079590 A1 Mar. 16, 2023

(30) Foreign Application Priority Data

Sep. 16, 2021 (TW) ................. 110134593

(51) Int. Cl.
*A61K 35/747* (2015.01)
*A61K 35/745* (2015.01)
*A61P 11/00* (2006.01)

(52) U.S. Cl.
CPC .......... *A61K 35/747* (2013.01); *A61K 35/745* (2013.01); *A61P 11/00* (2018.01)

(58) Field of Classification Search
CPC ...... A61K 35/747; A61K 35/745; A61P 11/00
USPC ...................................................... 424/93.45
See application file for complete search history.

(56) References Cited

U.S. PATENT DOCUMENTS

2016/0175429 A1* 6/2016 Benghezal .............. A61P 17/06
424/234.1
2019/0262408 A1* 8/2019 Maeda ................. A61K 35/745

FOREIGN PATENT DOCUMENTS

JP 2014003929 * 1/2014

OTHER PUBLICATIONS

Liu Y-W, Liao T-W, Chen Y-H, Chiang Y-C, Tsai Y-C (2014) Oral Administration of Heat-Inactivated Lactobacillus plantarum K37 Modulated Airway Hyperresponsiveness in Ovalbumin-Sensitized BALB/c Mice. PLoS One 9(6): e100105. doi:10.1371/journal.pone. 0100105 (Year: 2014).*
Wang X, Hui Y, Zhao L, Hao Y, Guo H, Ren F (2017) Oral administration of Lactobacillus paracasei L9 attenuates PM2.5-induced enhancement of airway hyperresponsiveness and allergic airway response in murine model of asthma. PLoS One 12(2): e0171721 . doi:10.1371/journal.pone.0171721 (Year: 2017).*
Qin, Fei et al. "Amelioration of Ambient Particulate Matter (PM2. 5)-Induced Lung Injury in Rats by Aerobic Exercise Training." Frontiers in physiology vol. 12 731594. Oct. 26, 2021, doi: 10.3389/fphys.2021.731594 (Year: 2021).*

* cited by examiner

*Primary Examiner* — Jennifer M. H. Tichy
(74) *Attorney, Agent, or Firm* — MH2 Technology Law Group, LLP (57) ABSTRACT

Disclosed herein is a method for preventing or alleviating particulate matter-induced lung injury. The method includes administering to a subject in need thereof a pharmaceutical composition including at least one heat-killed lactic acid bacterial strain that is selected from the group consisting of *Lactobacillus plantarum* CB102 which is deposited at the Deutsche Sammlung von Mikroorganismen und Zellkulturen (DSMZ) GmbH under an accession number DSM 33894, *Lactobacillus acidophilus* JCM 1132, *Bifidobacterium longum* CB108 which is deposited at the DSMZ GmbH under an accession number DSM 33895, *Bifidobacterium animalis* subsp. *lactis* JCM 10602, and combinations thereof.

3 Claims, 4 Drawing Sheets

METHOD FOR PREVENTING OR ALLEVIATING PARTICULATE MATTER-INDUCED LUNG INJURY

CROSS-REFERENCE TO RELATED APPLICATION

This application claims priority of Taiwanese Invention Patent Application No. 110134593, filed on Sep. 16, 2021.

FIELD

The present disclosure relates to a method for preventing or alleviating particulate matter-induced lung injury using at least one heat-killed lactic acid bacterial strain.

BACKGROUND

Atmospheric particulate matter, also known as particulate matter (PM) or fine particles, refers to microscopic solid or liquid particles suspended in the air, and is recognized as a major form of air pollution. Particulate matter can be distinguished into different sizes based on the aerodynamic diameter thereof, e.g., $PM_{10}$ and $PM_{2.5}$ refer to particulate matter having an aerodynamic diameter of ≤10 μm and ≤2.5 μm, respectively.

Particulate matter, which might consist of aromatic hydrocarbon, metallic material, mineral dust, organic toxins, etc., causes health problems due to its adverse effects on the respiratory system and the circulatory system. For example, particulate matter having an aerodynamic diameter ranging from 5 μm to 10 μm could accumulate in the bronchi, and particulate matter having an aerodynamic diameter ranging from 1 μm to 5 μm could invade the alveoli and then enters into the circulatory system through the alveolar capillaries, thereby causing systemic inflammation. Long-time exposure to particulate matter would cause lung injury including inflammatory damage, and would result in severe symptoms such as bronchial fibrosis, worsening of respiratory function, and impairment of lung immune system, among others.

Lactic acid bacteria (LAB) are gram-positive, lactic acid-producing bacteria that are conferred with the generally recognized as safe (GRAS) status, and are widely used as probiotics. Examples of common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies have reported that changes of microorganisms in the gastrointestinal tract and microbial metabolites closely correlates with immune response, inflammation, and progression of lung-related diseases. For example, diversity of probiotics in the gastrointestinal tract might alleviate symptoms of lung inflammation through regulation of cytokines produced by type 1 T helper (Th1) cells and type 2 T helper (Th2) cells (i.e., Th1/Th2 cytokine balance). Therefore, probiotics capable of regulating gut microbiota can be used to treat and/or prevent lung diseases.

However, a certain amount of probiotics, after administered orally, would be killed by gastric acid and bile salts respectively present in the stomach and duodenum, and the surviving probiotics would need to compete with pathogenic bacteria in the gastrointestinal tract before they are able to colonize and then proliferate therein. Hence, the amount of probiotics required to achieve the aforesaid beneficial effects might be difficult to be maintained. In addition, preservation of probiotics remains difficult because they are considered as "live microbial ingredient" of a food product, medicament or other consumable products.

SUMMARY

Therefore, the present disclosure provides a method for preventing or alleviating particulate matter-induced lung injury, which can alleviate at least one of the drawbacks of the prior art, and which includes administering to a subject in need thereof a pharmaceutical composition including at least one heat-killed lactic acid bacterial strain.

The at least one heat-killed lactic acid bacterial strain is selected from the group consisting of *Lactobacillus plantarum* CB102 which is deposited at the Deutsche Sammlung von Mikroorganismen und Zellkulturen (DSMZ) GmbH under an accession number DSM 33894, *Lactobacillus acidophilus* JCM 1132, *Bifidobacterium longum* CB108 which is deposited at the DSMZ GmbH under an accession number DSM 33895, *Bifidobacterium animalis* subsp. *lactis* JCM 10602, and combinations thereof.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of active components against lung injury induced by particulate matter, the applicant surprisingly found that, contrary to conventional teachings of using live microorganisms, certain heat-killed lactic acid bacterial strains are capable of modulating immune response by reducing the immunoglobulin E (IgE) concentration and increasing the type 1 T helper (Th1) cells/type 2 T helper (Th2) cells cytokine ratio in mice with particulate matter-induced lung injury, and hence is expected to be effective in preventing or alleviating such particulate matter-induced lung injury.

Therefore, the present disclosure provides a method for preventing or alleviating particulate matter-induced lung injury, which includes administering to a subject in need thereof a pharmaceutical composition including at least one heat-killed lactic acid bacterial strain.

The at least one heat-killed lactic acid bacterial strain is selected from the group consisting of *Lactobacillus plantarum* CB102 which is deposited at the Deutsche Sammlung von Mikroorganismen und Zellkulturen (DSMZ) GmbH under an accession number DSM 33894, *Lactobacillus acidophilus* JCM 1132, *Bifidobacterium longum* CB108 which is deposited at the DSMZ GmbH under an accession number DSM 33895, *Bifidobacterium animalis* subsp. *lactis* JCM 10602, and combinations thereof.

As used herein, the term "heat-killing" can be used interchangeably with other terms such as "heat inactivation", and refers to subjecting probiotics to a heat treatment for a predetermined time period so as to kill them.

The heat-killed lactic acid bacterial strain may be prepared using techniques well-known to those skilled in the art. In this regard, those skilled in the art may refer to journal articles, e.g., Segawa, S. et al. (2008), *Int. J. Food Microbiol.*, 128:371-377, and Ben Othman, M. et al. (2020), *Food Res. Int.*, 129:108792, doi:10.1016/j.foodres.2019.108792.

According to the present disclosure, the heat-killing may be performed by heating at a temperature ranging from 60° C. to 140° C. for a time period ranging from 1 second to 30 minutes. In an exemplary embodiment, the heat-killing is performed at a temperature of 73±2° C. for a time period of 15 seconds.

According to the present disclosure, the heat-killed lactic acid bacterial strain may be further subjected to a drying treatment using techniques well-known to those skilled in the art. Examples of the drying treatment may include, but are not limited to, a spray-drying treatment, a lyophilization treatment, a vacuum evaporation treatment, and combinations thereof. In an exemplary embodiment, the heat-killed lactic acid bacterial strain is further subjected to a spray-drying treatment.

According to the present disclosure, the heat-killed lactic acid bacterial strain, prior to being subjected to the drying treatment, is first subjected to a separation treatment so as to remove a culture medium used. In certain embodiments, the separation treatment may be selected from the group consisting of a centrifugation treatment, a filtration treatment, and a combination thereof. In an exemplary embodiment, the separation treatment is a centrifugation treatment.

As used herein, the term "preventing" or "prevention" means eliminating or reducing the incidence of particulate matter-induced lung injury in a subject not yet been diagnosed with particulate matter-induced lung injury, or slowing, delaying, controlling, or decreasing the likelihood or probability of particulate matter-induced lung injury in the subject.

As used herein, the term "alleviating" or "alleviation" refers to at least partially reducing, ameliorating, relieving, controlling, treating or eliminating one or more clinical signs of particulate matter-induced lung injury; and lowering, delaying, stopping or reversing the progression of severity regarding the condition or symptom of particulate matter-induced lung injury being treated.

As used herein, the term "particulate matter-induced lung injury" refers to an injury or damage to the lungs of a subject after exposure to particulate matter. Examples of the injury or damage may include, but are not limited to, inflammatory cell infiltration, interstitial thickening, structure distortion, abnormal collagen deposition, pulmonary fibrosis, and combinations thereof.

According to the present disclosure, the pharmaceutical composition may further include a pharmaceutically acceptable carrier, and may be made into a dosage form suitable for oral administration using techniques well-known to those skilled in the art.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Examples of the dosage form for oral administration may include, but are not limited to, sterile powders, tablets, troches, lozenges, pellets, capsules, dispersible powders or granules, solutions, suspensions, emulsions, drops, syrup, elixirs, slurry, and the like.

According to the present disclosure, the pharmaceutical composition may further include a probiotic microorganism selected from the group consisting of *Lactobacillus* spp., *Bifidobacterium* spp., *Bacillus* spp., *Streptococcus* spp., *Lactococcus* spp., *Abiotrophia* spp., *Aerococcus* spp., *Carnobacterium* spp., *Enterococcus* spp., *Leuconostoc* spp., *Oenococcus* spp., *Pediococcus* spp., *Tetragenococcus* spp., *Vagococcus* spp., *Weisella* spp., *Saccharomyces* spp., *Kluyveromyces* spp., *Staphylococcus* spp., *Propionibacterium* spp., and combinations thereof.

In certain embodiments, the probiotic microorganism is selected from the group consisting of *Bacillus coagulans* CB85 which is deposited at the DSMZ GmbH under an accession number DSM 33893, *Lactobacillus paracasei* JCM 8130, and a combination thereof.

As used herein, the terms "probiotic" and "probiotic microbes" are used interchangeably, and refer to preparations of live microorganisms. These microorganisms may remain and survive in the gastrointestinal tract after ingestion by a subject, and can exert a desired effect (e.g., adjusting the gut microbiota, preventive or therapeutic effect, etc.).

According to the present disclosure, a ratio of a number of the probiotic microorganism to that of the heat-killed lactic acid bacterial strain in the pharmaceutical composition may range from 1:0.5 to 1:5.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

The dose and frequency of administration of the pharmaceutical composition of the present disclosure may vary depending on the following factors: the severity of the illness or disorder to be treated, routes of administration, and weight, age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Lactic Acid Bacterial (LAB) Strains

The lactic acid bacterial (LAB) strains used in the following examples were obtained from the Department of Food Science and Biotechnology, National Chung-Hsing University, Taichung, Taiwan.

A. *Lactobacillus plantarum* CB102

*Lactobacillus plantarum* CB102 has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 910893 since May 8, 2019, and has also been deposited under the Budapest Treaty at the Deutsche Sammlung von Mikroorganismen und Zellkulturen (DSMZ) GmbH (Inhoffenstraße 7B, 38124 Braunschweig, Germany) under an accession number DSM 33894 since Jun. 9, 2021.

B. *Lactobacillus acidophilus* JCM 1132

*Lactobacillus acidophilus* JCM 1132, which is known and readily available to the public, has been deposited at the Japan Collection of Microorganisms (JCM) of the RIKEN BioResource Research Center (BRC), Microbe Division (3-1-1 Koyadai, Tsukuba, Ibaraki 305-0074, Japan), and has also been deposited at the DSMZ GmbH under an accession number DSM 20079.

C. *Lactobacillus paracasei* JCM 8130

*Lactobacillus paracasei* JCM 8130, which is known and readily available to the public, has been deposited at the JCM of the RIKEN BRC, and has also been deposited at the DSMZ GmbH under an accession number DSM 5622.

D. *Bifidobacterium longum* CB108

*Bifidobacterium longum* CB108 has been deposited at the BCRC of the FIRDI under an accession number BCRC 910894 since May 8, 2019, and has also been deposited under the Budapest Treaty at the DSMZ GmbH under an accession number DSM 33895 since Jun. 9, 2021.

E. *Bifidobacterium animalis* Subsp. *Lactis* JCM 10602

*Bifidobacterium animalis* subsp. *lactis* JCM 10602, which is known and readily available to the public, has been deposited at the JCM of the RIKEN BRC, and has also been deposited at the DSMZ GmbH under an accession number DSM 10140.

F. *Bacillus coagulans* CB85

*Bacillus coagulans* CB85 has been deposited at the BCRC of the FIRDI under an accession number BCRC 911010 since Jul. 23, 2020, and has also been deposited under the Budapest Treaty at the DSMZ GmbH under an accession number DSM 33893 since Jun. 9, 2021

2. Experimental Mice

Male C57BL/6J mice (6 weeks old, with a body weight of approximately 20±1 g) used in the following experiments were purchased from BioLasco Taiwan Co., Ltd. All the experimental mice were housed in an animal room with an independent air conditioning system under the following laboratory conditions: an alternating 12-hour light and 12-hour dark cycle, a temperature maintained at 22° C.±2° C., and a relative humidity maintained at 55%±5%. The mice were provided with water and fed ad libitum. All experimental procedures involving the experimental mice were in compliance with the legal provision of the Animal Protection Act of Taiwan, and were carried out according to the guidelines of the Animal Care Committee of the Council of Agriculture, Taiwan.

General Experimental Procedures:
1. Preparation of Viable Bacterial Suspension of LAB Strain A respective one of the six LAB strains as described in section 1 of the General Experimental Materials was inoculated into a BD Difco™ Lactobacilli MRS (De Man, Rogosa and Sharpe) broth (Catalogue no.: DF0881-17-5) supplemented with 0.05% (w/w) cysteine, and was then cultured at a temperature of 37° C. for 16 hours to obtain a respective one of LAB cultures. Next, each of the LAB cultures was subjected to centrifugation at 4° C. to form supernatant and pellet fractions. After that, the supernatant was poured off, and then the pellet was washed and resuspended in an appropriate amount of phosphate-buffered saline (PBS), thereby obtaining a bacterial suspension of the respective LAB strain. The bacterial suspensions of the aforesaid LAB strains were used in the following experiments.

2. Preparation of Heat-Killed Bacterial Suspension of LAB Strain

First, a respective one of the viable bacterial suspensions of *Lactobacillus plantarum* CB102, *Lactobacillus acidophilus* JCM 1132, *Bifidobacterium longum* CB108, and *Bifidobacterium animalis* subsp. *lactis* JCM 10602 as described in section 1 of the General Experimental Procedures was subjected to heat-killing using high-temperature short-time (HTST) pasteurization at 73° C.±2° C. for 15 minutes. Next, each of the heat-killed bacterial suspensions of *Lactobacillus plantarum* CB102, *Lactobacillus acidophilus* JCM 1132, *Bifidobacterium longum* CB108, and *Bifidobacterium animalis* subsp. *lactis* JCM 10602 was subjected to centrifugation at 25° C. under a speed of 10000 rpm for 15 minutes to form supernatant and pellet fractions. The resultant cell pellet was collected, followed by a spray-drying treatment, so as to obtain a respective one of spray-dried powders of *Lactobacillus plantarum* CB102, *Lactobacillus acidophilus* JCM 1132, *Bifidobacterium longum* CB108, and *Bifidobacterium animalis* subsp. *lactis* JCM 10602. The respective spray-dried powder was mixed with an appropriate amount of PBS, thereby obtaining a heat-killed bacterial suspension. The heat-killed bacterial suspensions of the aforesaid LAB strains were used in the following experiments.

3. Preparation of Particulate Matter (PM) Suspension

An appropriate amount of filter media with standard reference material (SRM) thereon (Sigma-Aldrich; Catalogue no.: NIST® SRM® 2783) was cut into several small pieces and then immersed in PBS. Thereafter, the filter media was subjected to ultrasonic treatment for 15 minutes, followed by centrifugation under a speed of 1000 rpm for 5 minutes to form supernatant and pellet fractions. Subsequently, the supernatant was collected and subjected to drying under reduced pressure, followed by resuspension in an appropriate amount of PBS, thereby obtaining a particulate matter suspension.

Example 1. Evaluation of the Effect of Heat-Killed LAB Strains on Particulate Matter-Induced Lung Injury In this example, the expression levels of immunoglobulin E (IgE), interferon-γ (IFN-γ) and interleukin-4 (IL-4) were determined as indicators of inflammation, so as to evaluate the effect of heat-killed LAB strains on particulate matter-induced lung injury.

Experimental Procedures:
A. Administration of Heat-Killed LAB Strain and Induction of Lung Injury by Particulate Matter The C57BL/6J mice as described in section 2 of the General Experimental Materials were randomly divided into a normal control group (NCG), a pathological control group (PCG), and four experimental groups (i.e., experimental groups 1 to 4 (EG1 to EG4)) (n=6 per group). The mice in the EG1 to EG4 were respectively fed, via oral gavage, with the heat-killed bacterial suspensions of *Lactobacillus plantarum* CB102, *Bifidobacterium longum* CB108, *Lactobacillus acidophilus* JCM 1132, and *Bifidobacterium animalis* subsp. *lactis* JCM 10602 prepared in section 2 of the General Experimental Procedures, at a concentration of $1.0 \times 10^7$ CFU/day per mouse. Each mouse was fed once daily for a total period of 14 days. In addition, the mice in each of the NCG and PCG were not subjected to any treatment.

On the fifteenth day after start of administering the aforesaid heat-killed bacterial suspensions, each mouse in the PCG and EG1 to EG4 was intranasally administered with 100 µL of the particulate matter suspension described in section 3 of the General Experimental Procedures (dose: 0.16 mg of PM per mouse). Each mouse was administered once daily for a total period of 3 days. In addition, the mice in the NCG were not subjected to any treatment.

B. Determination of Concentrations of IgE, IFN-γ and IL-4 in Mouse Lung Tissue

On the fourth day after start of administering the particulate matter suspension, the mice in each of the NCG, PCG, and EG1 to EG4 were sacrificed through $CO_2$ asphyxiation, and lung tissue was obtained from each mouse carcass. Next, the respective lung tissue was immersed in PBS, and was then subjected to ultrasonic vibration at 4° C. for 5 times (10 seconds for each time), followed by cooling on ice. After centrifugation at 4° C. under a speed of 1000 rpm for 15 minutes, the thus obtained supernatant fraction was subjected to determination of IgE, IFN-γ and IL-4 concentrations respectively using BD OptEIA™ Mouse IgE ELISA Set (Manufacturer: BD Biosciences; Catalogue No.: 555248), BD OptEIA™ Mouse IFN-γ ELISA Set (Manufacturer: BD Biosciences; Catalogue No.: 555138), and BD OptEIA™ Mouse IL-4 ELISA Set (Manufacturer: BD Biosciences; Catalogue No.: 555232) in accordance with the manufacturer's instructions. The thus obtained absorbance values of IgE, IFN-γ, and IL-4 of the mice in a respective one of the NCG, PCG, EG1 to EG4 were converted to their concentrations expressed in pg/mg according to standard curves prepared in advance using standards with different known concentrations of IgE, IFN-γ, and IL-4, respectively.

Subsequently, the concentration of IFN-γ of the respective one of the NCG, PCG, EG1, EG2, EG3 and EG4 was divided by the concentration of IL-4 of the same group, so as to calculate the type 1 T helper (Th1) cells/type 2 T helper (Th2) cells cytokine ratio (i.e., the Th1/Th2 cytokine ratio) in each group, which is known as the ratio of pro-inflammatory cytokine to anti-inflammatory cytokine.

Figure 1:
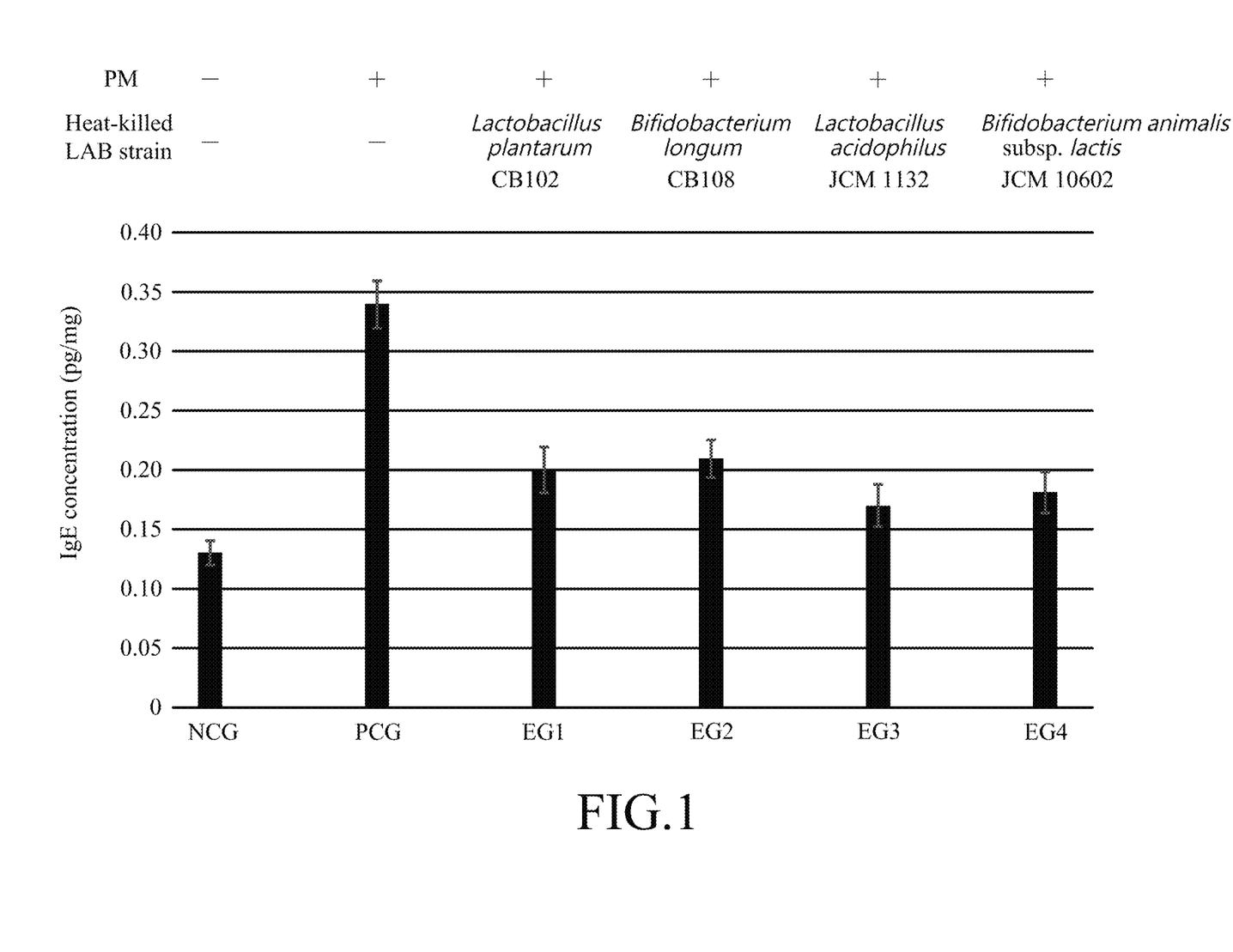
FIG. 1 shows the immunoglobulin E (IgE) concentration in the mice lung tissue in each group of Example 1, infra.

Results:

FIG. 1 shows the concentration of IgE in the mice lung tissue in each group. As shown in FIG. 1, the concentration of IgE determined in the PCG was significantly higher than that of the NCG, indicating that an inflammatory response was successfully induced by the particulate matter in the mice lung tissues. In addition, the concentration of IgE determined in each of the EG1 to EG4 was significantly lower as compared with that of the PCG.

Figure 2:
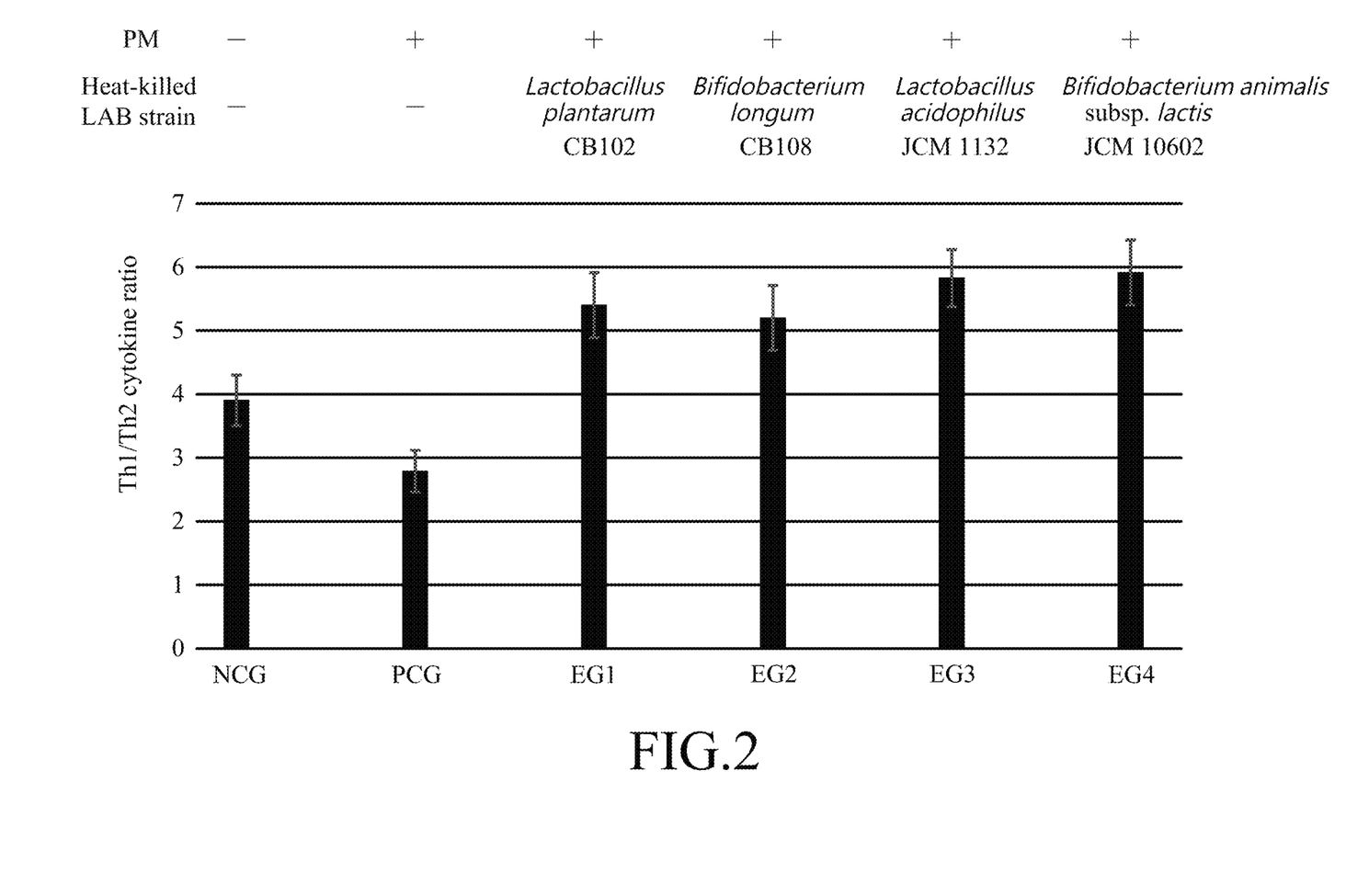
FIG. 2 shows the type 1 T helper (Th1) cells/type 2 T helper (Th2) cells cytokine ratio (Th1/Th2 cytokine ratio) in the mice lung tissue in each group of Example 1, infra.

FIG. 2 shows the Th1/Th2 cytokine ratio determined in the mice lung tissue in each group. As shown in FIG. 2, the Th1/Th2 cytokine ratio determined in the PCG was significantly lower than that of the NCG, indicating that an inflammatory response was successfully induced by the particulate matter in the mice lung tissues. In addition, the Th1/Th2 cytokine ratio determined in each of the EG1 to EG4 was significantly higher than that of the PCG.

These results demonstrate that the pretreatment with a respective one of the heat-killed *Lactobacillus plantarum* CB102, *Bifidobacterium longum* CB108, *Lactobacillus acidophilus* JCM 1132, and *Bifidobacterium animalis* subsp. *lactis* JCM 10602 can effectively protect the mice against inflammation in the lung tissue induced by particulate matter. Therefore, any one of the heat-killed *Lactobacillus plantarum* CB102, *Bifidobacterium longum* CB108, *Lactobacillus acidophilus* JCM 1132, and *Bifidobacterium animalis* subsp. *lactis* JCM 10602 is expected to be useful for effectively preventing or alleviating particulate matter-induced lung injury.

Example 2. Evaluation of the Effect of Combined Use of Heat-Killed LAB Strain and Viable LAB Strain on Particulate Matter-Induced Lung Injury Experimental Procedures:

The C57BL/6J mice as described in section 2 of the General Experimental Materials were randomly divided into a normal control group (NCG), a pathological control group (PCG), two comparative groups (i.e., comparative groups 1 to 2 (CG1 to CG2)), and eight experimental groups (i.e., experimental groups 1 to 8 (EG1 to EG8)) (n=6 per group). The mice in each of the CG1, CG2 and EG1 to EG8 were fed, via oral gavage, with the respective testing agent as shown in Table 1 below and as described in section 1 or 2 of General Experimental Procedures. Each mouse was fed once daily for a total period of 14 days. In addition, the mice in each of the NCG and PCG were not subjected to any treatment.

TABLE 1

| | Testing agent | | | | | |
|---|---|---|---|---|---|---|
| | Viable bacterial suspension of LAB strain (CFU/day) | | Heat-killed bacterial suspension of LAB strain (CFU/day) | | | |
| Group | *Bacillus coagulans* CB85 | *Lactobacillus paracasei* JCM 8130 | *Lactobacillus plantarum* CB102 | *Bifidobacterium longum* CB108 | *Lactobacillus acidophilus* JCM 1132 | *Bifidobacterium animalis* subsp. *lactis* JCM 10602 |
| NCG | — | — | — | — | — | — |
| PCG | — | — | — | — | — | — |
| CG1 | $6.8 \times 10^6$ | — | — | — | — | — |
| CG2 | — | $6.8 \times 10^6$ | — | — | — | — |

TABLE 1-continued

| | Testing agent | | | | | |
|---|---|---|---|---|---|---|
| | Viable bacterial suspension of LAB strain (CFU/day) | | Heat-killed bacterial suspension of LAB strain (CFU/day) | | | |
| Group | Bacillus coagulans CB85 | Lactobacillus paracasei JCM 8130 | Lactobacillus plantarum CB102 | Bifidobacterium longum CB108 | Lactobacillus acidophilus JCM 1132 | Bifidobacterium animalis subsp. lactis JCM 10602 |
| EG1 | $3.4 \times 10^6$ | — | $5.0 \times 10^6$ | — | — | — |
| EG2 | — | $3.4 \times 10^6$ | $5.0 \times 10^6$ | — | — | — |
| EG3 | $3.4 \times 10^6$ | — | — | $5.0 \times 10^6$ | — | — |
| EG4 | — | $3.4 \times 10^6$ | — | $5.0 \times 10^6$ | — | — |
| EG5 | $3.4 \times 10^6$ | — | — | — | $5.0 \times 10^6$ | — |
| EG6 | — | $3.4 \times 10^6$ | — | — | $5.0 \times 10^6$ | — |
| EG7 | $3.4 \times 10^6$ | — | — | — | — | $5.0 \times 10^6$ |
| EG8 | — | $3.4 \times 10^6$ | — | — | — | $5.0 \times 10^6$ |

On the fifteenth day after start of administering the aforesaid testing agents, each mouse in the PCG, CG1, CG2, and EG1 to EG8 was intranasally administered with 100 μL of the particulate matter suspension described in section 3 of the General Experimental Procedures (dose: 0.16 mg of PM per mouse). Each mouse was fed once daily for a total period of 3 days. In addition, the mice in the NCG were not subjected to any treatment.

After that, the concentrations of IgE, IFN-γ and IL-4 in the mice lung tissue and the resultant Th1/Th2 cytokine ratio in a respective one of the NCG, PCG, CG1, CG2, and EG1 to EG8 were determined according to the method described in section B of Example 1.

Figure 3:
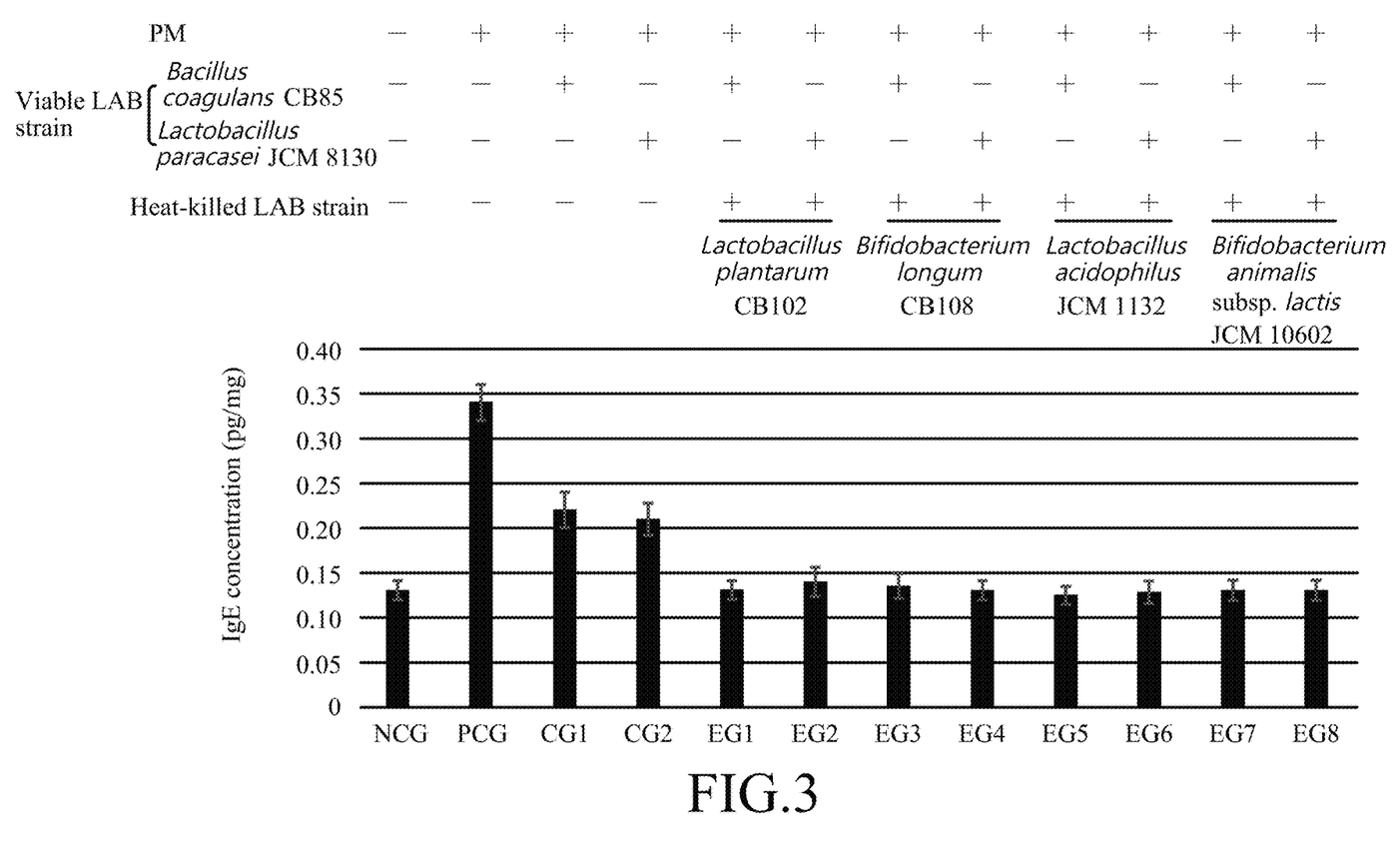
FIG. 3 shows the IgE concentration in the mice lung tissue in each group of Example 2, infra.

Results:

FIG. 3 shows the concentration of IgE in the mice lung tissue in each group. As shown in FIG. 3, the concentration of IgE determined in the PCG was significantly higher than that of the NCG, indicating that an inflammatory response was successfully induced by the particulate matter in the mice lung tissue. In addition, the concentration of IgE determined in each of the CG1, CG2, and EG1 to EG8 was significantly lower as compared with that of the PCG, and the degree of decrease in IgE concentration in each of the EG1 to EG8 was greater compared with that in the CG1 and CG2. In particular, the concentration of IgE determined in each of the EG1 to EG8 was substantially similar to that of the NCG.

Figure 4:
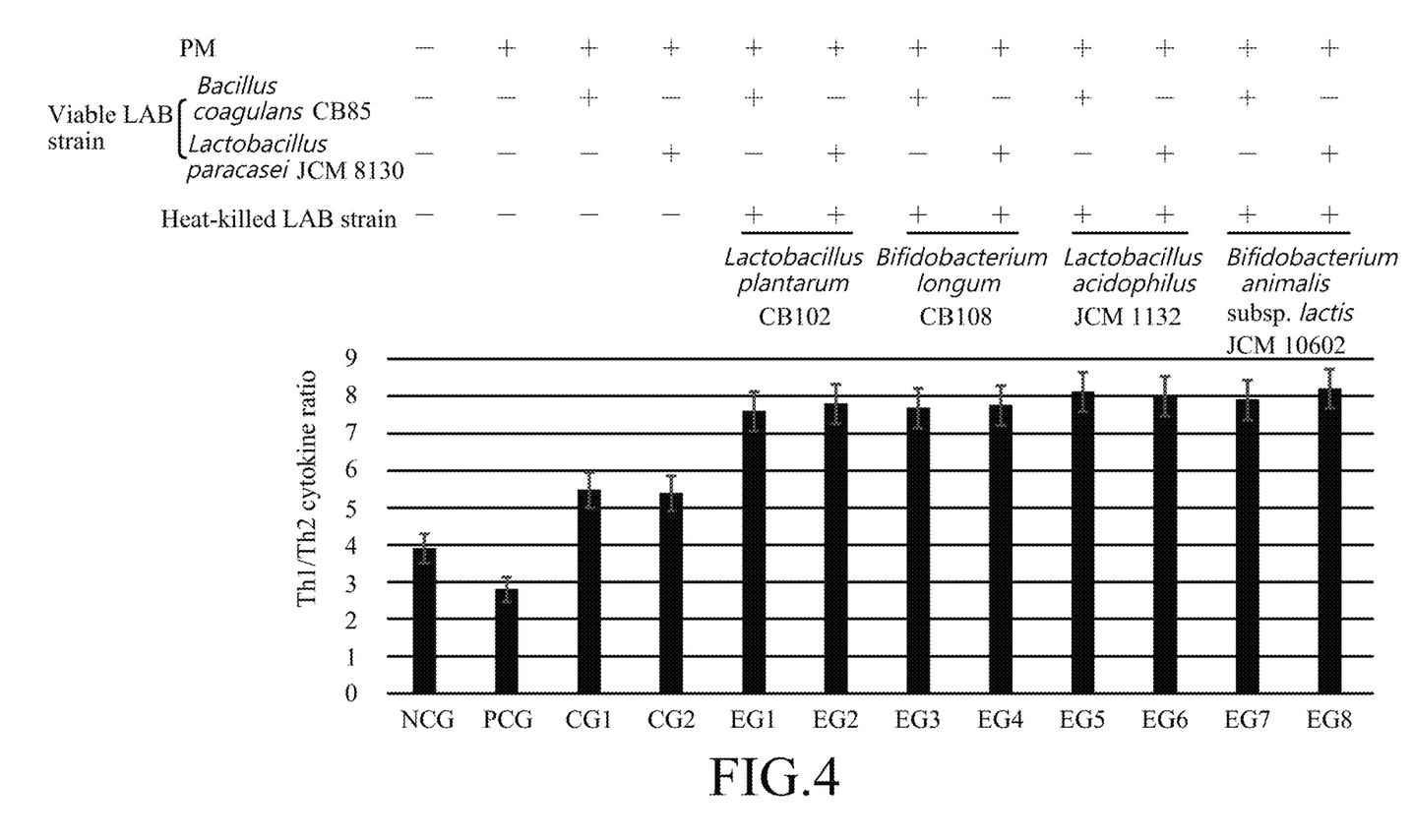
FIG. 4 shows the Th1/Th2 cytokine ratio in the mice lung tissue in each group of Example 1, infra.

FIG. 4 shows the Th1/Th2 cytokine ratio determined in the mice lung tissue in each group. As shown in FIG. 4, the Th1/Th2 cytokine ratio determined in the PCG was significantly lower than that of the NCG, indicating that an inflammatory response was successfully induced by the particulate matter in the mice lung tissue. In addition, the Th1/Th2 cytokine ratio determined in each of the CG1, CG2, and EG1 to EG8 was significantly higher than that of the PCG, and the degree of increase in the Th1/Th2 cytokine ratio in each of the EG1 to EG8 was greater compared with that in the CG1 and CG2.

In addition, the results in FIGS. 3 and 4 show that, the degree of decrease in IgE concentration and the degree of increase in Th1/Th2 cytokine ratio in the EG1, EG3, EG5 and EG7 relative to the PCG were respectively greater than those in the CG1 relative to the PCG, while the degree of decrease in IgE concentration and the degree of increase in Th1/Th2 cytokine ratio in the EG2, EG4, EG6 and EG8 relative to the PCG were respectively greater than those in the CG2 relative to the PCG, suggesting that a mixture containing one of the aforesaid heat-killed LAB strains and one of the aforesaid viable LAB strains can greatly enhance the efficacy of inhibiting lung inflammation in mice.

These results demonstrate that the pretreatment with a mixture containing a respective one of the four heat-killed LAB strains (i.e., Lactobacillus plantarum CB102, Bifidobacterium longum CB108, Lactobacillus acidophilus JCM 1132, and Bifidobacterium animalis subsp. lactis JCM 10602) and a respective one of the two viable LAB strains (i.e., Bacillus coagulans CB85 and Lactobacillus paracasei JCM 8130) can effectively protect the mice against inflammation in the lung tissue induced by particulate matter. Therefore, the aforesaid mixture is expected to be useful for effectively preventing or alleviating particulate matter-induced lung injury.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating particulate matter-induced lung injury, comprising administering to a subject in need thereof a pharmaceutical composition including at least one heat-killed lactic acid bacterial strain and a probiotic microorganism, wherein the at least one heat-killed lactic acid bacterial strain is selected from the group consisting of *Lactobacillus plantarum* CB102 which is deposited at the Deutsche Sammlung von Mikroorganismen und Zellkulturen (DSMZ) GmbH under an accession number DSM 33894, *Lactobacillus acidophilus* JCM 1132, *Bifidobacterium longum* CB108 which is deposited at the DSMZ GmbH under an accession number DSM 33895, *Bifidobacterium animalis* subsp. *lactis* JCM 10602, and combinations thereof, wherein the probiotic microorganism is selected from the group consisting of *Bacillus coagulans* CB85 which is deposited at the DSMZ GmbH under an accession number DSM 33893, *Lactobacillus paracasei* JCM 8130, and a combination thereof, and wherein a ratio of a number of the probiotic microorganism to that of the heat-killed lactic acid bacterial strain in the pharmaceutical composition ranges from 1:0.5 to 1:5.

2. The method as claimed in claim 1, wherein the pharmaceutical composition further includes a pharmaceutically acceptable carrier.

3. The method as claimed in claim 1, wherein the pharmaceutical composition is in a dosage form for oral administration.

* * * * *